United States Patent [19]

Kelly

[11] Patent Number: 4,488,872
[45] Date of Patent: Dec. 18, 1984

[54] ORTHODONTIC LINGUAL FACE BOW

[76] Inventor: Vincent M. Kelly, 4550 S. Harvard, Tulsa, Okla. 74135

[21] Appl. No.: 572,759

[22] Filed: Jan. 23, 1984

[51] Int. Cl.³ .............................................. A61C 7/00
[52] U.S. Cl. ..................................................... 433/5
[58] Field of Search ........................................... 433/5

[56] References Cited

U.S. PATENT DOCUMENTS 4,229,165 10/1980 Kurz ..................................... 433/5
4,431,410 2/1984 Ruderman ............................. 433/5

Primary Examiner—Robert Peshock
Attorney, Agent, or Firm—Head, Johnson & Stevenson

[57] ABSTRACT

An orthodontic face bow lever arm for applying torque to a lingual or palatal side orthodontic appliance comprising a rigid (e.g., hard acrylic) tray with an inner softer surface (e.g., thermoplastic) contoured to act as a cushioned fulcrum pivoting about the teeth wherein a pair of wire lever arms are embedded in the rigid hard acrylic portion. The intraoral extension of the wire lever arms terminate in a hook that fits between the teeth and the archwire of the lingual orthodontic appliance while the extraoral extension of the wire lever arms project outwardly and upwardly terminating in a second set of hooks which attach elastically to a conventional high pull orthodontic headgear. Such a face bow is particularly useful in applying a lever arm torque effect to the lingual appliance, thus forcing the root of the tooth rearward (i.e., tooth root tips back).

4 Claims, 5 Drawing Figures

4,488,872

ORTHODONTIC LINGUAL FACE BOW

BACKGROUND OF THE INVENTION

1. Field of the Invention:

This invention relates to an improved orthodontic face bow. More specifically, this invention relates to a lingual orthodontic face bow and torquing lever arm.

2. Description of the Prior Art:

The general concept of mounting an orthodontic appliance involving anchoring bands or the like to either the outer surface, the inner surface or both surfaces of the teeth and then applying tension or other force as a corrective treatment for malocclusion and for minor tooth movement is now a common, well accepted procedure. It is also generally known and a common accepted practice to provide various headgear apparatus and elastic tensioning means (e.g., rubber bands) with various types of so-called face bows or night braces to apply force selectively to the orthodontic appliance attached to the teeth. However, usually these face bows are employed such as to make contact with buccal tubes secured to the teeth in conjunction with visible braces mounted to the outer surface of the teeth as opposed to lingual or braces mounted exclusively to the backside of the teeth. Thus, for example, U.S. Pat. Nos. 3,337,958; 3,303,566 4,087,915 and 4,224,022 disclose various orthodontic face bows which involve the use of the intraoral inner blow that engages to the buccal tubes thus forcing the conventional non-lingual brace rearward.

SUMMARY OF THE INVENTION

In view of the prior art, I have discovered a lingual orthodontic face bow lever arm comprising:

(a) an essentially rigid tray means contoured to rest and pivot on at least one tooth, thus serving as the fulcrum of the face bow lever arm;

(b) a first wire lever arm embedded within the tray means and extending both intraoral and extraoral from the tray means, wherein the intraoral extension consists of the first wire extending essentially parallel to the backside of the tooth and terminating with a hook means that fits between a tooth and lingual archwire attached to the teeth and wherein the extraoral extension consists of the first wire extending outwardly and upwardly terminating in a fastener means adapted to engage to a high pull headgear that applies torque through the first wire lever arm to the lingual archwire; and (c) a second wire lever arm embedded within the tray means and extending both intraoral and extraoral from the tray means, wherein the intraoral extension consists of the second wire extending essentially parallel to the backside of the tooth and terminating with a hook means that fits between a tooth and lingual archwire attached to the teeth and wherein the extroaral extension consists of the second wire extending outwardly and upwardly terminating in a fastener means adapted to engage to a high pull headgear that applies torque through the second wire lever arm to the lingual archwire.

The present invention further provides for an extraoral support element, e.g., a soldered wire, to rigidly attach the first wire lever arm to the second. In one preferred embodiment, the tray acting as the fulcrum is formed from hard acrylic in which the wires are embedded, and the inner surface of the tray making contact with the surface of the teeth is coated with a softer material, e.g., soft acrylic or thermoplastic.

It is an object of the present invention to provide an orthodontic face bow that can be used to create a rearward torquing force on the lingual or palatal side of a lingual orthodontic archwire or the like that tends to tip the root of the tooth rearward. It is a further object to provide a lingual orthodontic face bow that creates the desired rearward force by a lever arm action when attached or engaged to a conventional elastic or other type of headgear. Fulfillment of these objects and the presence and fulfillment of additional objects will become apparent upon complete reading of the specification and claims taken in conjunction with the attached drawings.

DESCRIPTION OF THE PREFERRED EMBODIMENTS

Figure 1:
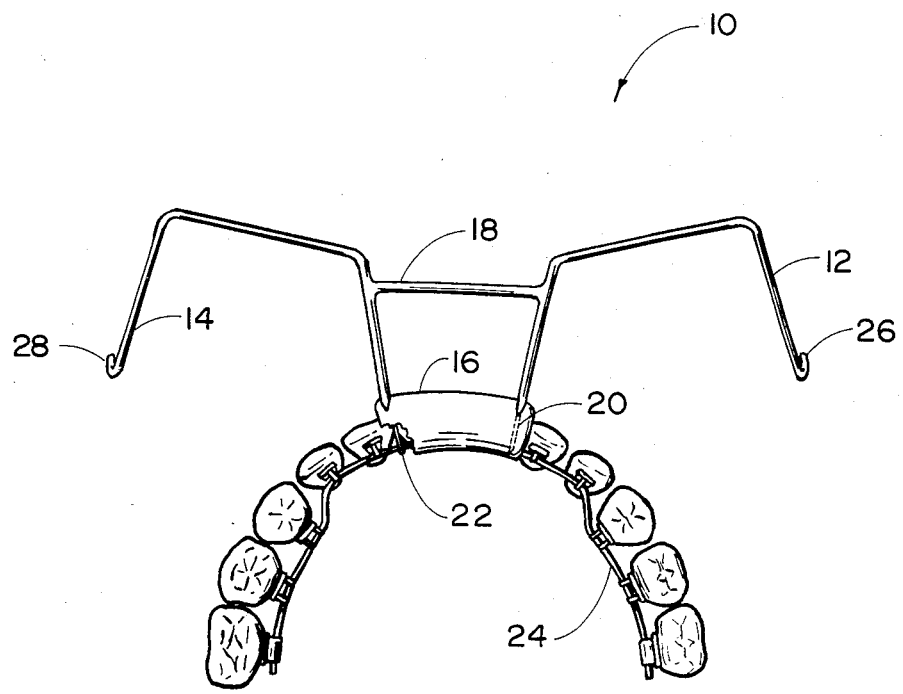
FIG. 1 illustrates a cut-away view of a set of teeth with lingual orthodontic appliance attached and a lingual orthodontic lever arm according to the present invention engaged to this appliance.

The improved lingual orthodontic face bow lever arm according to the present invention, how it functions and the advantages of its use as well as how it differs relative to the prior art devices can perhaps be best explained and understood by reference to the attached drawings. FIG. 1 illustrates a partial cut-away view of a set of teeth with a lingual orthodontic appliance attached to the backside of the teeth thus making the braces essentially invisible. FIG. 1 further shows a lingual orthodontic face bow and torquing lever arm according to the present invention, generally designated by the numeral 10. This face bow 10 involves a pair of lever arm wires 12 and 14 which are embedded in a piece of rigid plastic 16 that rests directly on the front incisors. In order to enhance the structural rigidity and stability of the face bow 10, an optional extraoral wire support element 18 is soldered between the lever arm wires 12 and 14. The lever arm wires 12 and 14 upon passing through the plastic tray 16 bend behind the teeth and terminate at a pair of hooks 20 and 22. As further illustrates in FIG. 1, the intraoral extensions of wires 12 and 14 with hooks 20 and 22 are designed to fit between the tooth and lingual brace or orthodontic appliance 24. Thus, the hooks 20 and 22 reversibily attach to the lingual brace 24. The other, extraoral, ends of wires 12 and 14 terminate in a second pair of hooks 26 and 28.

Figure 2:
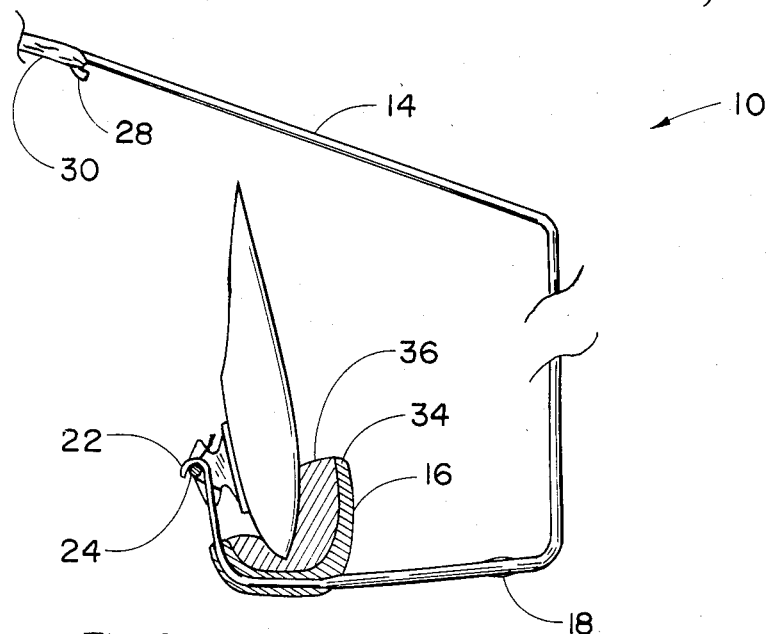
FIG. 2 is a side view of the lingual orthodontic appliance of FIG. 1 being held under tension by the rubber bands of a conventional high pull head harness.
Figure 3:
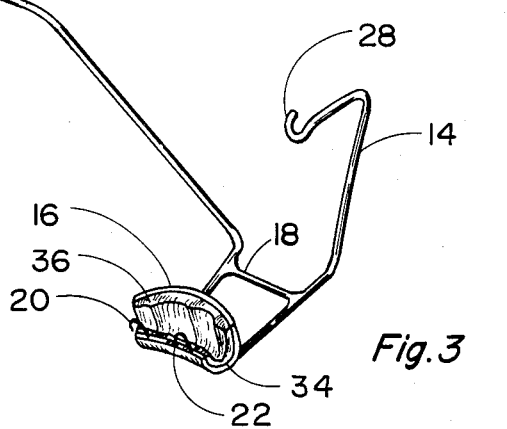
FIG. 3 is a top view of the lingual orthodontic lever arm of FIG. 1 removed from the orthodontic appliance.
Figure 5:
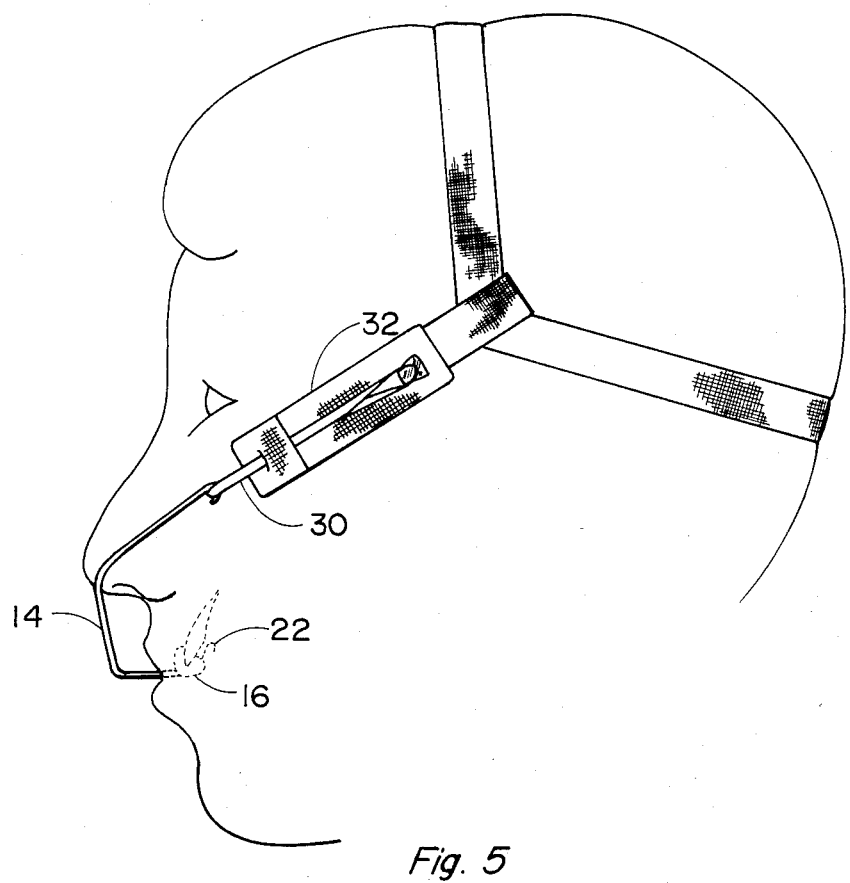
FIG. 5 illustrates the use of the lingual orthodontic appliance with a high pull elastic headgear according to the present invention.

As seen in FIG. 2, the lingual orthodontic face bow 10 during use involves the incisors resting directly in contact with an inner softer layer 36 molded to the more rigid outer layer 34 of the plastic tray 16. This inner softer layer 36 which makes contact with the teeth preferably is molded to fit the specific contours of the user's teeth as shown in FIG. 3. As further illustrated in FIG. 2, the support wire 14 passes through the more rigid layer 34 of plastic tray 16 terminating at the lingual end with hook 22 engaged to lingual brace 24 and at the extraoral end with hook 28 being held under elastic tension by rubber band 30 of a conventional head harness or the like (see FIG. 5). Similarly, the support wire 12, hook 20 and hook 28 (not visible in this side view) pass through the rigid tray layer 34, attached to lingual brace 24 and is held under rubber band tension, respectively, as would be viewed from the other side. By applying elastic tension through the rubber bands or the like of the head harness, the wire arms apply a lever arm torque to the intraoral portion of wire 12 and 14 by virtue of tray 16 acting as a lever arm fulcrum or pivot surface. This lever arm torque in turn creates the desired rearward force on the lingual brace 24 and consequently assists in the ultimate desired lingual movement or repositioning of root tips of the teeth attached to the lingual appliance 24.

It is envisioned that the rearward force being created by this lever arm torquing technique is compatible with a variety of already existing and commercially available lingual orthodontic braces and appliances. Furthermore, the specific point of application of force can be selected and controlled by the respective geometry of the intraoral portion of the lever arm wires as well as the position of attachment of the lingual orthodontic applicance to the teeth. Thus, the contact point for application of the force can be easily distributed further back along the lingual brace and in fact, can be made essentially equivalent to the known buccal tube engagement if necessary, but on the inner side of the teeth. Furthermore, it is envisioned that various types of fasteners and corresponding lingual appliance engagement mechanisms can be readily incorporated into the overall design of the face bow and as such, should be considered equivalent for purposes of this invention.

Figure 4:
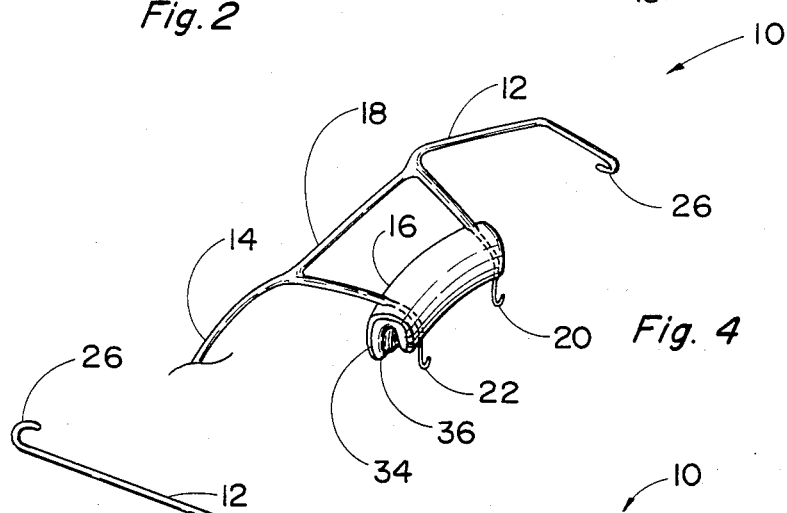
FIG. 4 is a bottom view of the lingual orthodontic lever arm of FIG. 1 removed from the orthodontic appliance.

FIGS. 3 and 4 further illustrate the lingual orthodontic face bow lever arm 10 of FIG. 1 removed from the lingual appliance. As illustrated in these figures, the respective hooks at the ends of the wires 12 and 14 are intentionally configured to assist the user in inserting and removing the device from between the brace and teeth as well as for ease of snapping on and off the rubber bands of the headgear. It should be further obvious that the extraoral portion of the wire can be bent and shaped to fit generally any of the headgear equipment as well known in the art. The rigid tray element that serves as the fulcrum of the lever arm motion is preferably contoured to rest and pivot on the front teeth of the user. As seen in FIG. 3, a shallow valley with upturned edges can be employed to allow for user comfort, yet reduce the risk of misalignment or slippage. FIGS. 3 and 4 also illustrate the preferred concept of providing a rigid exterior layer 34 preformed with lever arm wires 12 and 14 embedded therein and an interior or pivot surface 36 making contact with the teeth. As previously indicated, this interior surface 36 is intentionally molded out of a softer material than the rigid layer 34 and is shaped to conform to the surface of the teeth to which it makes contact.

The lever arm face bow according to the present invention can be made out of essentially any material well known in the art by essentially any of the techniques or methods employed to make conventional face bows. Similarly, the support tray member making contact with the teeth can be made out of any rigid material used for such purposes, preferably a hard acrylic, epoxy, fiber reinforced thermoplastic or the equivalent is used either by itself of preferably in combination with a softer inner surface composition such as soft acrylic, thermoplastics, elastomeric compositions or the like.

Having thus described the preferred embodiments with a certain degree of particularity, it is manifest that many changes can be made in the details of construction, arrangement and fabrication of the elements and their uses without departing from the spirit and scope of this invention. Therefore, it is to be understood that the invention is not limited to the embodiments set forth herein for purposes of exemplification, but is to be limited only by the scope of the attached claims, including a full range of equivalents to which each element thereof is entitled.

I claim:

1. A lingual orthodontic face bow lever arm comprising:
   (a) an essentially rigid tray means contoured to rest and pivot on at least one tooth, thus serving as the fulcrum of said face bow lever arm;
   (b) a first wire lever arm embedded within said tray means and extending both intraoral and extraoral from said tray means, wherein said intraoral extension consists of said first wire extending essentially parallel to the backside of the tooth and terminating with a hook means that fits between a tooth and lingual archwire attached to the teeth and wherein said extraoral extension consists of said first wire extending outwardly and upwardly terminating in a fastener means adapted to engage to a high pull headgear that applies torque through said first wire lever arm to the lingual archwire; and
   (c) a second wire lever arm embedded within said tray means and extending both intraoral and extraoral from said tray means, wherein said intraoral extension consists of said second wire extending essentially parallel to the backside of the tooth and terminating with a hook means that fits between a tooth and lingual archwire attached to the teeth and wherein said extraoral extension consists of said second wire extending outwardly and upwardly terminating in a fastener means adapted to engage to a high pull headgear that applies torque through said second wire lever arm to the lingual archwire.

2. A lingual orthodontic face bow lever arm of claim 1 further comprising an extraoral support element rigidly attaching said first wire lever arm to said second wire lever arm.

3. A lingual orthodontic face bow lever arm of claim 2 wherein said essentially rigid tray means is formed from hard acrylic on the exterior and within which said wire lever arms are embedded and a soft interior making pivotal contact with the tooth.

4. A lingual orthodontic face bow lever arm of claim 3 wherein said soft interior making pivotal contact with the tooth is molded such as to fit the contour of the tooth.

* * * * *